(12) United States Patent
Winiski et al.

(10) Patent No.: US 9,085,763 B2
(45) Date of Patent: Jul. 21, 2015

(54) **TISSUE MORPHOLOGY PRODUCED WITH THE FUNGUS *PYCNOPORUS CINNABARINUS***

(71) Applicants: Jacob Michael Winiski, Troy, NY (US); Sue Sweet Van Hook, Cambridge, NY (US)

(72) Inventors: Jacob Michael Winiski, Troy, NY (US); Sue Sweet Van Hook, Cambridge, NY (US)

(73) Assignee: Ecovative Design LLC, Green Island, NY (US)

( * ) Notice: Subject to any disclaimer, the term of this patent is extended or adjusted under 35 U.S.C. 154(b) by 0 days.

(21) Appl. No.: 14/048,652

(22) Filed: Oct. 8, 2013

(65) Prior Publication Data

US 2014/0120602 A1    May 1, 2014

Related U.S. Application Data

(60) Provisional application No. 61/720,428, filed on Oct. 31, 2012.

(51) Int. Cl.
*C12N 1/14* (2006.01)
*C12R 1/645* (2006.01)
*C12N 1/22* (2006.01)

(52) U.S. Cl.
CPC ... *C12N 1/14* (2013.01); *C12N 1/22* (2013.01)

(58) Field of Classification Search
None
See application file for complete search history.

*Primary Examiner* — Ruth Davis
*Assistant Examiner* — Emily Cordas
(74) *Attorney, Agent, or Firm* — Francis C. Hand; Carella, Byrne, et al.

(57) ABSTRACT

Methods are provided for producing the following tissue characteristics via environmental and chemical manipulation of the vegetative and fruiting phases of the Basidiomycete fungus *Pycnoporus cinnabarinus*:

1) Aerial vegetative mycelium pigmented with cinnabarinic acid;
2) Aerial vegetative mycelium without pigmentation;
3) A resupinate fruiting body pore surface pigmented with cinnabarinic acid; and
4) Thickened masses of vegetative aerial mycelium.

8 Claims, 5 Drawing Sheets

TISSUE MORPHOLOGY PRODUCED WITH THE FUNGUS *PYCNOPORUS CINNABARINUS*

This application claims the benefit of Provisional Patent Application 61/720,428 filed Oct. 31, 2012.

This invention relates to a tissue morphology produced with the fungus *Pycnoporus cinnabarinus*

BACKGROUND OF THE INVENTION

*Pycnoporus cinnabarinus* (*P. cinnabarinus*) is a saprophytic basidiomycete within the family polyporaceae. *P. cinnabarinus* is a primary white-rot decomposer of hardwood and produces bright orange semicircular basidiocarps from Spring through Fall and has been observed that basidiocarps are primarily found in open spaces with ample light exposure.

Unique characteristics of the *P. cinnabarinus* species include production of the orange pigment cinnabarinic acid in both the mycelium and fruiting body, as well as utilization of the economically important enzyme laccase as a primary lignin degrading enzyme.

Commercial attention has been primarily focused on exploiting *P. cinnabarinus* as a producer of laccase and various other enzymes and proteins as well as the ability of *P. cinnabarinus* to degrade bioactive compounds rather than the specific morphologies and aesthetics of the tissue of *P. cinnabarinus*.

As is known, *P. cinnabarinus* production of the phenoxazinone derivative cinnabarinic acid is dependent on laccase oxidation of the precursor 3-hydroxyanthranilic acid. Several stimuli of laccase activity have been reported including copper.

Observations of the inventors showed a connection of the expression of cinnabarinic acid and subsequent pigmentation to light exposure.

Accordingly, it is an object of the invention to provide a material produced with the mycelium tissue of the Basidiomycete fungus *Pycnoporus cinnabarinus*.

It is another object of the invention to provide a packaging element having a surface with cushioned protrusions thereon.

It is another object of the invention to provide a packaging element having a cushioned surface.

It is another object of the invention to provide a process of making packaging elements with dense fluffy surfaces.

It is another object of the invention to provide a buoyant element that is self-colorized.

SUMMARY OF THE INVENTION

Briefly, in one embodiment, *P. cinnabarinus*'s ability to self-colorize by producing cinnabarinic acid allows for the production of an orange-red material without the use of other pigments. A specific application example would be marine buoys, in which pigmentation with a bright, high-saturation, environmentally safe pigment is desirable.

The invention provides an element having a morphology (i.e. form and structure) that may be described as a self-supporting composite structure having discrete particles of lignocellulose and a network of interconnected mycelia cells of *P. cinnabarinus* extending through and around the discrete particles of lignocellulose to bond the discrete particles together as well as mycelia cells on the surface of the composite structure consisting of vegetative mycelium pigmented with cinnabarinic acid or a resupinate pore surface.

As is known, the *P. cinnabarinus* species typically produces a three-dimensional shelf mushroom extending from the mycelium mass with the underside of the mushroom consisting of a pore surface. A resupinate pore surface is when the fungus expresses only a pore surface over the two-dimensional surface of the mycelium mass rather than forming a three-dimensional fruit body.

Through control of specific stimuli—light, CO2, and relative humidity—it is possible to control if/when/how the tissue (mycological material) is pigmented. Exposure of a vegetative mycelium to the daylight spectrum of light results in pigmentation, whereas incubation in the absence of light represses pigmentation.

Further, reducing CO2 in conjunction with reducing relative humidity results in a pigmented resupinate pore surface, which is unique in producing a matte surface (i.e. a surface without a shine or glossiness) and rich coloration.

It may also be possible to catalyze the formation of cinnabarinic acid via stimulating laccase with copper.

In another embodiment, the invention provides an element having a morphology (i.e. form and structure) that provides an ideal protective and cushioned surface for packaging purposes.

The invention also provides methods for producing the following tissue characteristics via environmental and chemical manipulation of the vegetative and fruiting phases of the Basidiomycete fungus *Pycnoporus cinnabarinus*:

1) Aerial vegetative mycelium pigmented with cinnabarinic acid;
2) Aerial vegetative mycelium without pigmentation;
3) A resupinate fruiting body pore surface pigmented with cinnabarinic acid; and
4) Thickened masses of vegetative aerial mycelium.

These and other objects and advantages of the invention will become more apparent from the following detailed description taken in conjunction with the drawings wherein.

EXAMPLE 1

In this embodiment, the process of making the element may be characterized as an aerial vegetative mycelium pigmented with cinnabarinic acid. This process includes the steps of inoculating a substrate, such as a mass of discrete particles of lignocellulose, with *P. cinnabarinus* spawn [step 1—see FIG. 4]. In this process, an "aerial vegetative mycelium" means that the hyphal cells of the mycelium grow out from the surface of the mass of lignocellulose resulting in a "fluffy" surface.

Next, the inoculated lignocellulose is placed in a mold with the shape of the element to be produced.

The mold is then placed in an environment consisting of $CO_2$ above 2%, and preferably 5%, a relative humidity above 95%, and preferably 99%, a temperature of from 50° F. to 90° F., and preferably 72° F., and with indirect exposure to light, such as the daylight spectrum of light. [step 2a] and incubated until the lignocellulose mass has been fully colonized by the fungus. During this time, a verification step may be performed to verify that all surfaces in which aerial vegetative mycelium is desired are unobstructed and interfacing with the environment.

The term "fully colonized" means that a network of interconnected mycelia cells of *P. cinnabarinus* extends through and around the discrete particles of lignocellulose to bond the discrete particles together into a self-supporting structure.

Incubation is continued for a period of 3 to 5 days until the desired tissue morphology has been achieved, i.e. a pigmented aerial vegetative mycelium. [step 3a].

In this embodiment, the element 10 has an orange-red pigmentation caused by the exposure of the vegetative mycelium (*P. cinnabarinus*) to light, such as daylight. That is to say, the element 10 is self-colorized. The term "self-colorized" as used herein means that the block 10 is colored by the ingredients used to make the block 10 during the process of manufacture without the use of other pigments.

Alternatively, if the form were produced via extrusion molding or other casting method the process would be applicable.

EXAMPLE 2

In this embodiment, the process of making the element may be characterized as an aerial vegetative mycelium without pigmentation. This process includes the same steps as in Example 1 except that all light is completely blocked from the incubation environment. For example, the inoculated lignocellulose is placed in a mold with a cover, or otherwise placed in a darkened incubation environment, such as a rack covered with black plastic to block out light.

EXAMPLE 3

Figure 1:
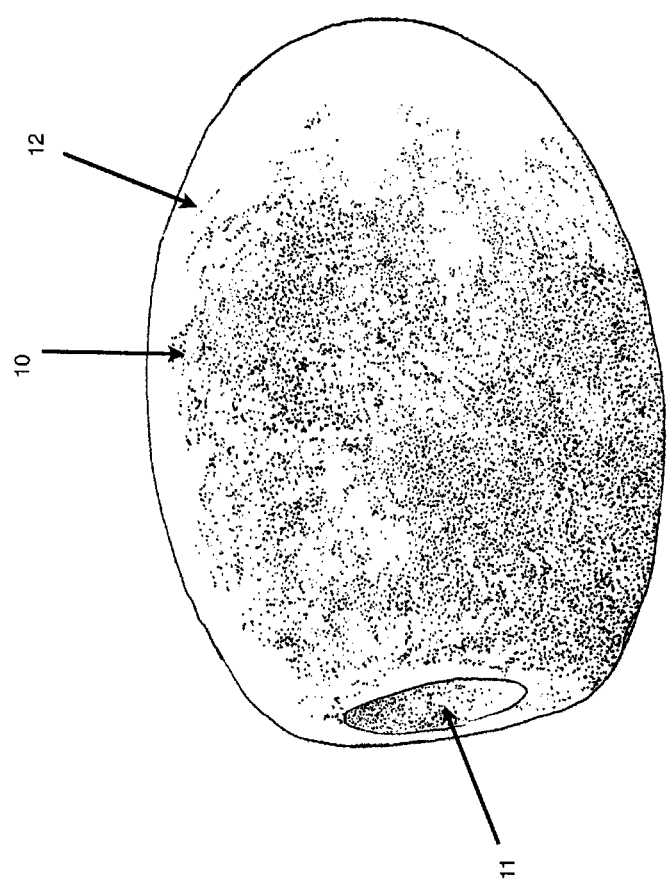
FIG. 1 illustrates a perspective view of a pigmented marine buoy produced in accordance with the invention.

Referring to FIG. 1, the buoyant element 10 is in the shape of a marine buoy of oblong shape with a central bore 11 and having external surfaces 12 with a pigmentation produced by cinnabarinic acid.

In this embodiment, the process of making the element 10 may be characterized as providing a pigmented resupinate fruiting body pore surface. This process includes the steps, as above, of inoculating a substrate, such as a mass of discrete particles of lignocellulose, with *P. cinnabarinus* spawn [step 1]; placing the inoculated lignocellulose in an environment consisting of $CO_2$ above 2%, and preferably 5%, a relative humidity above 95%, and preferably 99%, a temperature of 72° F., and with indirect exposure to light [step 2a]; and incubating until the lignocellulose mass has been fully colonized by the fungus [step 3a]

In this embodiment, the inoculated lignocellulose is placed in a mold with the shape of a buoy to be produced and with a removable plug to form the central bore 11

Thereafter, the environmental conditions of step 2 are changed to normal atmospheric $CO_2$, below 95% relative humidity and ideally 95% relative humidity, 72° F. temperature and indirect exposure to light. [step 3c]. Incubation is continued until the surfaces of the colonized lignocellulose mass interfacing with the external environment have differentiated into pigmented resupinate fruiting body pore surfaces. [step 4c]

EXAMPLE 4

Figure 2:
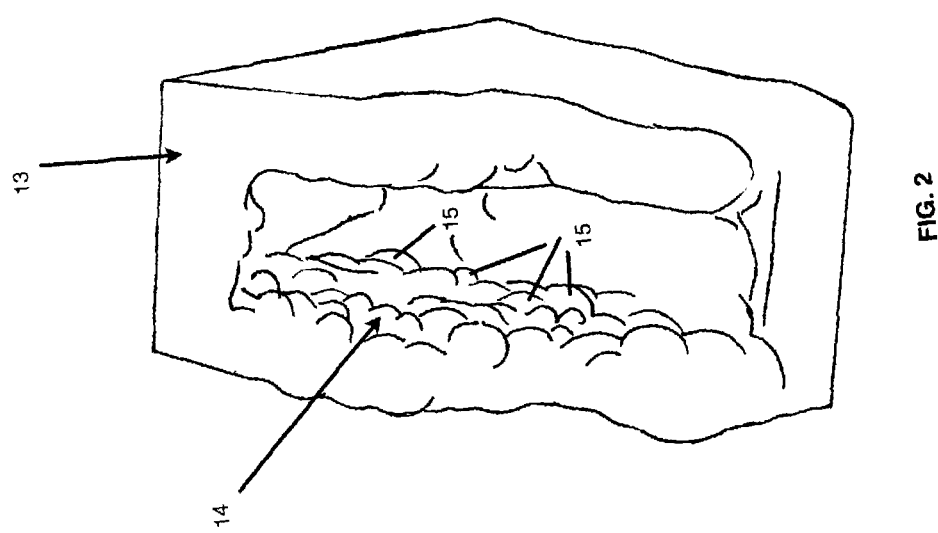
FIG. 2 illustrates a perspective view of an element with a fluffy surface in accordance with the invention.

Referring to FIG. 2, the element 13 has a "fluffy" surface 14.

In this embodiment, the process of making the element 13 may be characterized as providing a colonized lignocellulose element with a "fluffy" surface 14 composed and formed of thickened masses of aerial vegetative mycelium extending from an otherwise flat surface. The "fully" surface is distinguished from the "fuzzy" surface produced in Example 1 by the presence of thickened masses of aerial vegetative mycelium.

The process of forming the element 13 includes steps [1], [2a] and [3a] of Example 1 or Example 2 described above.

After the fungus has fully colonized the lignocellulose mass, verification is made that the surfaces where thickened masses of vegetative aerial mycelium are desired are interfacing with the external environment. Incubation is then continued for an additional 3 to 20 days beyond full substrate colonization [step 4ab] until the desired tissue morphology has been achieved, i.e. the formation of thickened masses of vegetative aerial mycelium 15 on the exterior surface(s) of the fully colonized the lignocellulose mass. [step 5ab]

This process results in a product that may be characterized as a fully colonized substrate having a cushioned, non-abrasive surface 14 formed by the thickened masses of vegetative aerial mycelium 15.

If the process exposes the lignocellulose mass to light, the resulting product has external surfaces pigmented with cinnabarinic acid. If the process does not expose the lignocellulose mass to light, the resulting product has no pigmentation produced by cinnabarinic acid.

Thus, the elements produced with *P. cinnabarinus*, when given an extended incubation period, develop cushioned protrusions (i.e. thickened masses of vegetative aerial mycelium) on the element surface, which may provide an ideal protective surface for packaging and other products requiring such a characteristic.

Elements produced with surface growth in environments with high relative humidity and high atmospheric $CO_2$ produce a dense, "fluffy" surface defined by extremely aerial vegetative hyphal growth. This again may provide an ideal protective/cushioned surface.

EXAMPLE 5

Figure 3:
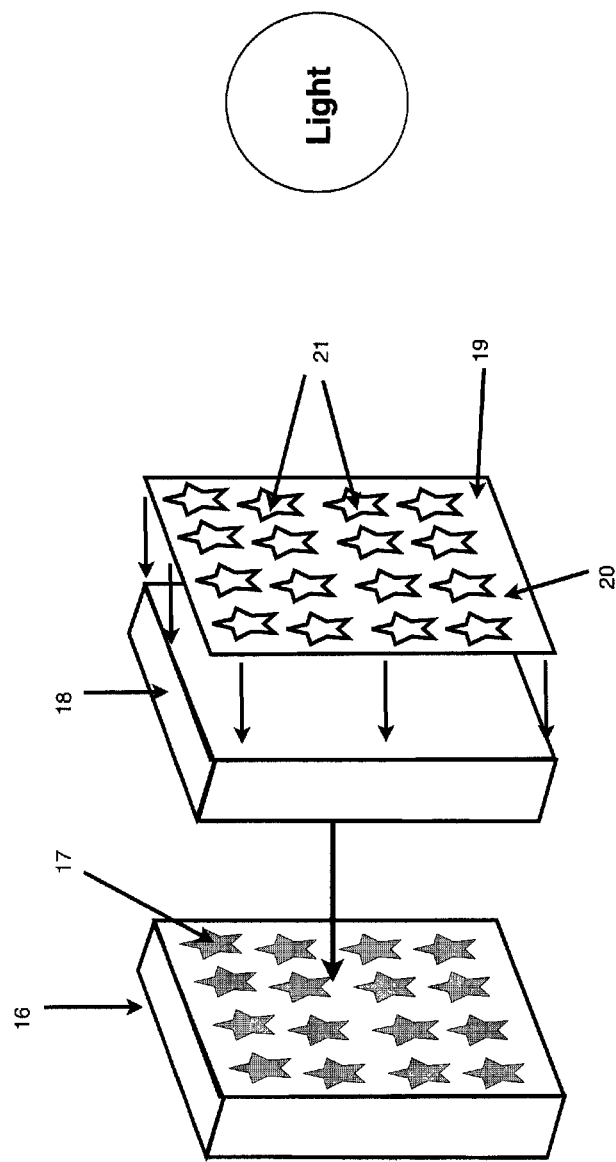
FIG. 3 is a schematic view of a process for imparting a specific pattern on the surface of an element in accordance with the invention.

Referring to FIG. 3, the element 16 is provided with a patterned surface 17.

In this embodiment, the process of making the element 16 may be characterized as imparting a specific pattern on the element (tissue) surface by stimulation of pigmentation.

This process includes the steps of inoculating a substrate, such as a mass of discrete particles of lignocellulose, with *P. cinnabarinus* spawn [step 1]; placing the inoculated lignocellulose in a mold and in an environment consisting of $CO_2$ above 2%, and preferably 5%, a relative humidity above 95%, and preferably 99%, a temperature of 72° F., and blocking out all light until a part 18 has been produced with non-pigmented mycelial tissue (i.e. myceliated lignosecellulose).

Next, a template 19 is placed on a tissue surface of the part 18 in which negative space(s) 20 of the desired pattern covers the tissue and positive space(s) 21 exposes the tissue.

The surface of the tissue (part 18) with the template 19 thereon is exposed to daylight while continuing to incubate in the environmental conditions of step 2 until the exposed portions of the tissue are pigmented due to the exposure of the vegetative mycelium to the light.

The template 18 is thereafter removed leaving the element 16 with the patterned surface 17 dictated by the template 18.

EXAMPLE 6

In this embodiment, the process may be characterized as stimulation of pigmentation with copper (Cu) and particularly a solution of copper sulfate ($CuSO_4$).

This process follows the steps of Example 1 or Example 2 and has the following options:

Option 1: Supplement the lignocellulose substrate with at least 0.2 ml/L $CuSO_4$ of total moisture content at or prior to inoculation [step 2d]

Option 2: During incubation, mist the tissue surfaces in which pigmentation is desired with a solution of at least 0.2 ml $CuSO_4$/1 L $H_2O$ [step 2e]

Option 3: Between steps 3 and 4 of Example 1, submerge the colonized lignocellulose in a solution of at least 0.2 ml $CuSO_4$/1 L $H_2O$ [step 3f]

Figure 4:
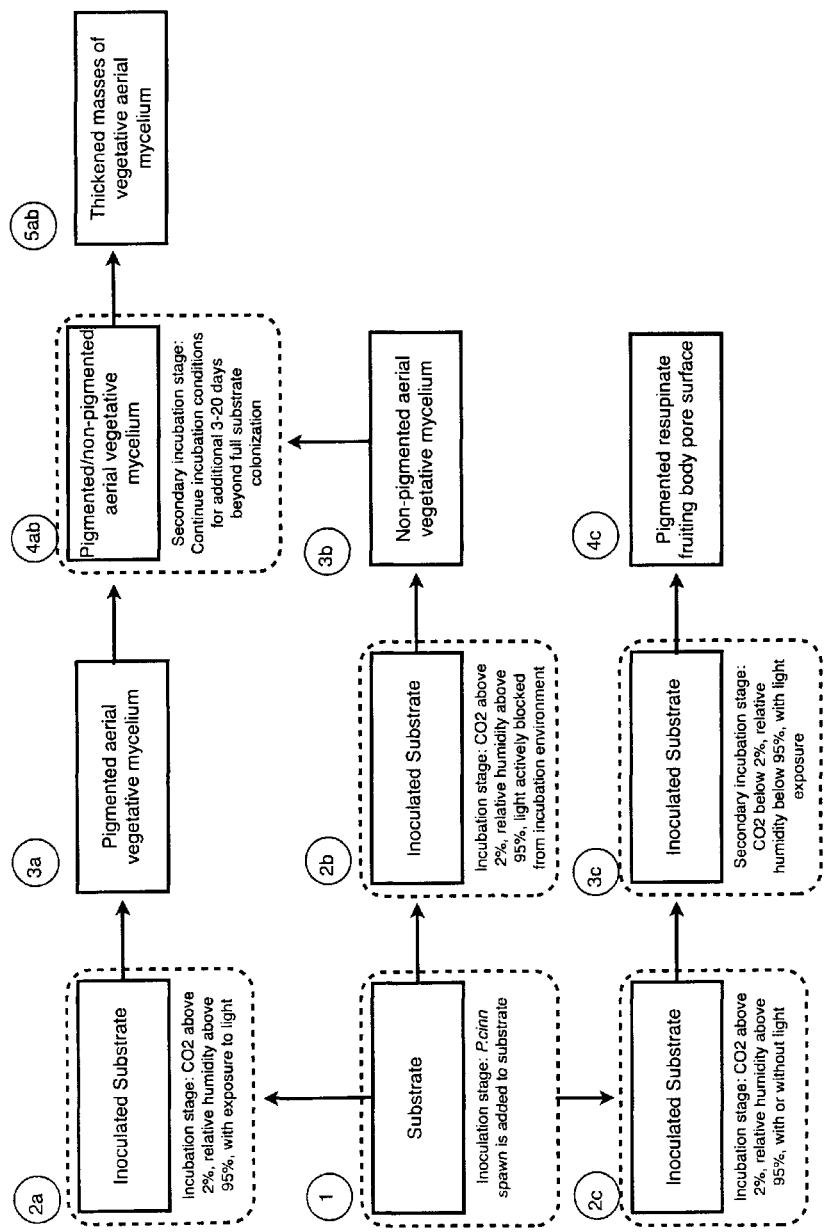
FIG. 4 is a schematic view of the various process steps of the invention.
Figure 5:
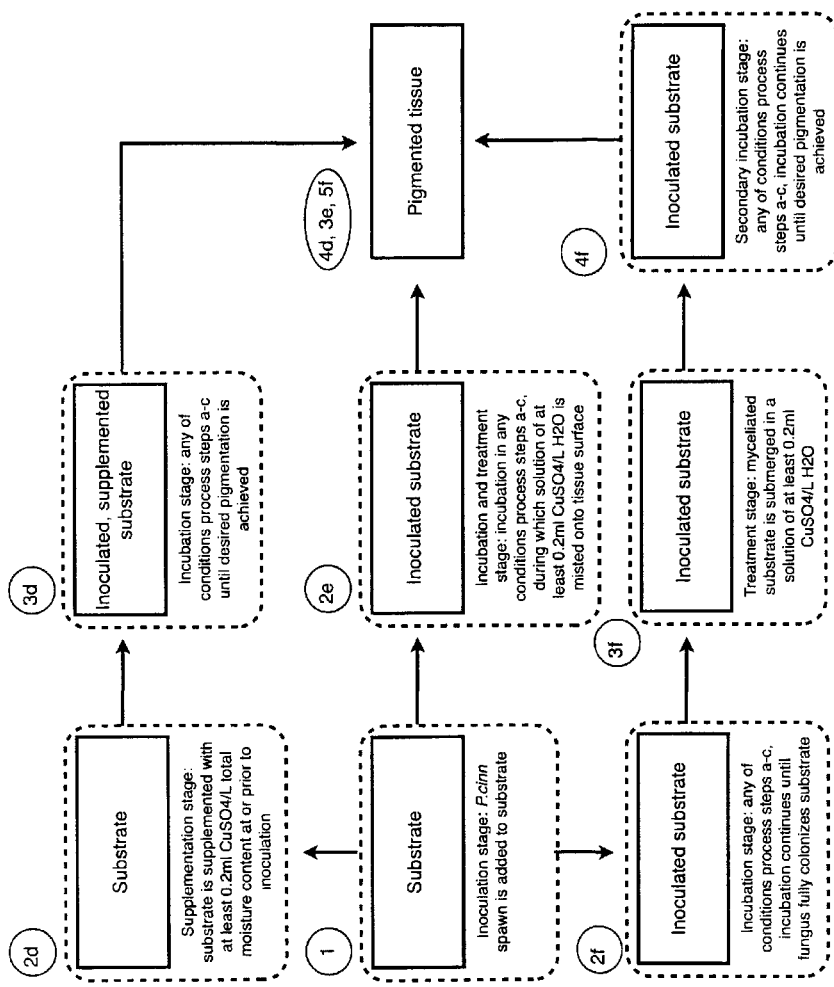
FIG. 5 is a further view of the various process steps of the invention.

Referring to FIGS. 4 and 5, the various steps of the processes described above may be combined in various selected manners to produce the desired product, i.e. a pigmented tissue [steps 4d, 3e, 5f], a non-pigmented aerial vegetative mycelium [step 3b], an element with a pigmented resupinate fruiting body pore surface [step c], an element with a surface formed of thickened masses of vegetative aerial mycelium [step 5ab].

Thus, the invention provides a material produced with the mycelium tissue of the Basidiomycete fungus *Pycnoporus cinnabarinus* that can be used for multiple purposes and particularly to provide a packaging element having a cushioned surface.

The invention also provides a product having dense fluffy surfaces as well as a product that can have a pigmented surface.

What is claimed is:

1. A method comprising the steps of
   inoculating a substrate of discrete particles of lignocellulose with *Pycnoporus cinnabarinus* spawn;
   placing the inoculated lignocellulose in an environment consisting of $CO_2$ above 2%, a relative humidity above 95%, a temperature of from 50° F. to 90° F.; and
   incubating the inoculated lignocellulose substrate for a time sufficient to fully colonize said substrate with *P. cinnabarinus* thereby forming a network of interconnected mycelia cells of *P. cinnabarinus* extending through and around said discrete particles of lignocellulose to bond said discrete particles together into a self-supporting structure thereof.

2. A method as set forth in claim 1 further comprising the steps of exposing the inoculated lignocellulose in said environment to indirect light and incubating for a period of time sufficient for a pigmented aerial vegetative mycelium to be produced on an external surface of said self-supporting structure.

3. A method as set forth in claim 2 wherein said environment has a $CO_2$ content of 5% and a relative humidity of 99%.

4. A method as set forth in claim 2 further comprising the step of adding copper to said substrate to increase laccase expression and stimulate pigmentation.

5. A method as set forth in claim 1 further comprising adjusting said environment to consist of $CO_2$ below 2% and a relative humidity below 95%, exposing the inoculated lignocellulose in said environment to indirect light, and incubating for a period of time sufficient to develop a pigmented resupinate fruiting body pore surface on an external surface of said self-supporting structure.

6. A method as set forth in claim 1 further comprising incubating for a period of time sufficient to develop a surface with thickened masses of vegetative aerial mycelium on an external surface of said self-supporting structure.

7. A method as set forth in claim 6 wherein said period of time is from 3 to 20 days.

8. A method as set forth in claim 6 wherein said thickened masses of vegetative aerial mycelium protrude outwardly from said surface to form a cushioned surface.

* * * * *